(12) United States Patent
Bryant

(10) Patent No.: US 11,337,876 B2
(45) Date of Patent: May 24, 2022

(54) HOSPITAL BED SHIELD

(71) Applicant: V. Tyronne Bryant, Grove City, OH (US)

(72) Inventor: V. Tyronne Bryant, Grove City, OH (US)

( * ) Notice: Subject to any disclaimer, the term of this patent is extended or adjusted under 35 U.S.C. 154(b) by 0 days.

(21) Appl. No.: 17/385,583

(22) Filed: Jul. 26, 2021

(65) Prior Publication Data

US 2022/0023128 A1 Jan. 27, 2022

Related U.S. Application Data

(60) Provisional application No. 63/056,763, filed on Jul. 27, 2020.

(51) Int. Cl.
| | | |
|---|---|---|
| *A61B 46/10* | (2016.01) | |
| *A61B 46/20* | (2016.01) | |
| *A61G 7/05* | (2006.01) | |
| *A61G 10/00* | (2006.01) | |

(52) U.S. Cl.
CPC ............ *A61G 10/005* (2013.01); *A61B 46/10* (2016.02); *A61G 7/05* (2013.01)

(58) Field of Classification Search
CPC ......... A61B 46/10; A61G 7/05; A61G 10/005
USPC ....... 55/385.1, 385.2; 95/273, 287; 128/847, 128/863
See application file for complete search history.

(56) References Cited

U.S. PATENT DOCUMENTS

| | | | | |
|---|---|---|---|---|
| 3,724,172 | A * | 4/1973 | Wood ..................... | A61G 10/02 95/287 |
| 4,140,105 | A * | 2/1979 | Duvlis ................ | A61G 13/108 128/847 |
| 6,039,776 | A * | 3/2000 | Liue .................... | A24F 19/0042 55/385.1 |
| 6,702,662 | B2 * | 3/2004 | Kristensson ............ | F24F 3/163 454/187 |
| 6,916,238 | B2 * | 7/2005 | Korman ................. | A61G 10/04 454/187 |
| 8,066,802 | B2 * | 11/2011 | Kristensson ......... | A61G 13/108 95/273 |
| 8,414,671 | B2 * | 4/2013 | Augustine ............ | A47C 21/044 55/385.2 |
| 8,444,747 | B2 * | 5/2013 | Kristensson ............. | F24F 11/30 95/14 |
| 2003/0033790 | A1 * | 2/2003 | Hague .................... | B01D 46/10 55/385.1 |
| 2008/0020695 | A1 * | 1/2008 | Chang .................. | B08B 15/026 454/56 |
| 2008/0092909 | A1 * | 4/2008 | Hahne ................ | A41D 13/1192 128/863 |
| 2010/0233019 | A1 * | 9/2010 | Al-Thallab ............... | F24F 3/16 422/4 |
| 2011/0126498 | A1 * | 6/2011 | Polsky ............... | G01R 33/0047 55/385.2 |

(Continued)

*Primary Examiner* — Minh Chau T Pham
(74) *Attorney, Agent, or Firm* — Steven A. Hill

(57) ABSTRACT

A transparent article of manufacture with improved and convenient access ports, light weight, venting, and ready for quick deployment. It may be single-use or reusable (upon proper sanitation). It has a vent for removal of aerosolized bacterial and viruses, and ports for clinicians to insert their hands. The general pyramidal shape promotes air flow to the vent, where aerosolized bacteria and viruses may be safely expelled, and allows for stacking.

5 Claims, 7 Drawing Sheets

(56) References Cited

U.S. PATENT DOCUMENTS

| | | | |
|---|---|---|---|
| 2012/0024154 A1* | 2/2012 | Augustine | A47C 21/044 |
| | | | 95/273 |
| 2017/0145711 A1* | 5/2017 | Esses | E04H 15/02 |
| 2017/0354143 A1* | 12/2017 | Rolfe | B32B 27/08 |
| 2021/0244594 A1* | 8/2021 | Dougherty | A61G 12/00 |

* cited by examiner

HOSPITAL BED SHIELD

CROSS-REFERENCE TO RELATED APPLICATIONS

This application claims the benefit of U.S. Provisional Application No. 63/056,763, titled "HOSPITAL BED SHIELD" filed Jul. 27, 2020.

STATEMENT REGARDING FEDERALLY SPONSORED RESEARCH OR DEVELOPMENT

This work was partially funded by the U.S. Department of Defense

REFERENCE TO SEQUENCE LISTING, A TABLE, OR A COMPUTER PROGRAM LISTING COMPACT DISK APPENDIX

Not Applicable

FIELD OF THE TECHNOLOGY

The subject technology is in the technical field of protective equipment for medical care providers.

BACKGROUND OF THE TECHNOLOGY

Intubation is an extreme measure that required in extraordinary conditions to provide lifesaving oxygen to a patient. Its use and potential consequences are so severe that laws allow patents to decline its use, via advance directives specifically stating that the patient is not to be intubated. (A "do not resuscitate" order covers chest compressions, cardiac drugs, and intubation. A "do not intubate" order allows chest compressions and cardiac drugs, but not intubation.)

Intubation, where the patient may expel virus and bacteria into the air, creates a hazard for clinicians performing the operation. The coronavirus pandemic beginning in the year 2019 has emphasized that risk, where thousands of physicians and others had died from exposure to the coronavirus from patients. As a result, physician Hsien Yung Lai, of Taiwan, is generally credited with creating a basic design for an intubation box or shield, to protect healthcare providers for aerosolized bacteria and viruses during intubation. [see the article at sites.google.com/view/aerosolbox/design]. The basic design has been released under a noncommercial license [see Creative Commons Attribution-NonCommercial 4.0 International License, creativecommons.org/licenses/by-nc/4.0/], and various commercial alternatives exist.

Current designs tend to be box shaped, and assembled from commonly available materials, cut to form various parts. They tend to be heavy materials, such as plexiglass, other heavy plastic materials, or glass. Key to all is transparency so that the clinicians may see the patient inside. They tend to be primarily reusable, requiring cleaning and storage. The subject technology is an improvement.

SUMMARY OF THE TECHNOLOGY

The subject technology is a transparent article of manufacture with improved and convenient access ports, light weight, venting, and ready for quick deployment. It may be single-use or reusable (upon proper sanitation). It has a vent, generally on top to facilitate air flow, for removal of aerosolized contaminants such as bacteria and viruses, and ports for clinicians to insert their hands. The general shape promotes air flow to the vent, where aerosolized bacteria, viruses, and carbon dioxide may be safely expelled. The general pyramidal shape allows for stacking, thusly providing convenience in storage and shipping.

DETAILED DESCRIPTION OF THE TECHNOLOGY

The following table identifies various elements discussed in the detail description of the drawings.

| | |
|---|---|
| 100 | shield |
| 102 | vent |
| 103 | top cap |
| 104 | side port |
| 105 | O-ring |
| 106 | drape coupling |
| 107 | locking ear |
| 108 | opening |
| 109 | port |
| 110 | rib |
| 111 | filter |
| 114 | hole |
| 120 | rear port |
| 122 | brim |
| 124 | notch |
| 202 | patient |

The following definitions apply:
"Brim" 122 is a support structure allowing the shield to rest upon a surface, such as a hospital bed.
"Drape coupling" 106 is a mechanism for fastening a cloth, plastic, or other pliable material to the shield, allowing a drape or curtain to be deployed to provide loose closure of opening.
A "filter" 111 is a material which inhibits the passage of aerosolized bacteria, viruses, and other contaminants.
A "locking ear" 107 is a ramp secured to the underside of the top cap 103, which engages with a corresponding reversely oriented ramp secured to the vent 102, so that when the top cap 103 is inserted onto the vent 102 and then rotated, the locking ear slides against the corresponding reversely oriented ramp. As a result, the top cap 103 is secured to the vent Turning the top cap 103 in the opposite direction releases the engagement with the corresponding reversely oriented ramp and the top cap 103 can then be removed.
"Notch" 124 is an opening through which ventilator tubing and other medically required tubing or cabling may pass into the interior of the shield 100.
An "O-ring" 103 is a pliable material uses as a gasket, generally shaped as the letter "O." "Side port" 104 is a portal, on left and right side, through which assistant clinicians may insert their hands to assist a primary clinician in the placement and operation of ventilation and other equipment on the patient 202.

"Rear port" 120 is a single, elongated port sufficiently dimensioned to allow a primary clinician to place two hands and forearms into shield 100, for proper placement and operation of ventilation and other equipment on the patient 202.

"Rib" 110 is an indentation or protrusion providing rigidity to a vacuum formed structure. Several are deployed in the subject technology.

"Top cap" 103 is a removable cover over the vent 102, through which air inside the shield 100 is removed from the patient 202.

As an article of manufacture, shield 100 is formed via a mold applied to plastic sheets (such as PETG which is a glycol modified version of Polyethylene Terephthalate (PET), further treated and embedded with antimicrobial material. Treated plastic sheets are heated and vacuum formed around a mold. The result is trimmed, and ports and other features are cut into it, resulting in the shield 100 as described in the words below and associated Figures.

Figure 1:
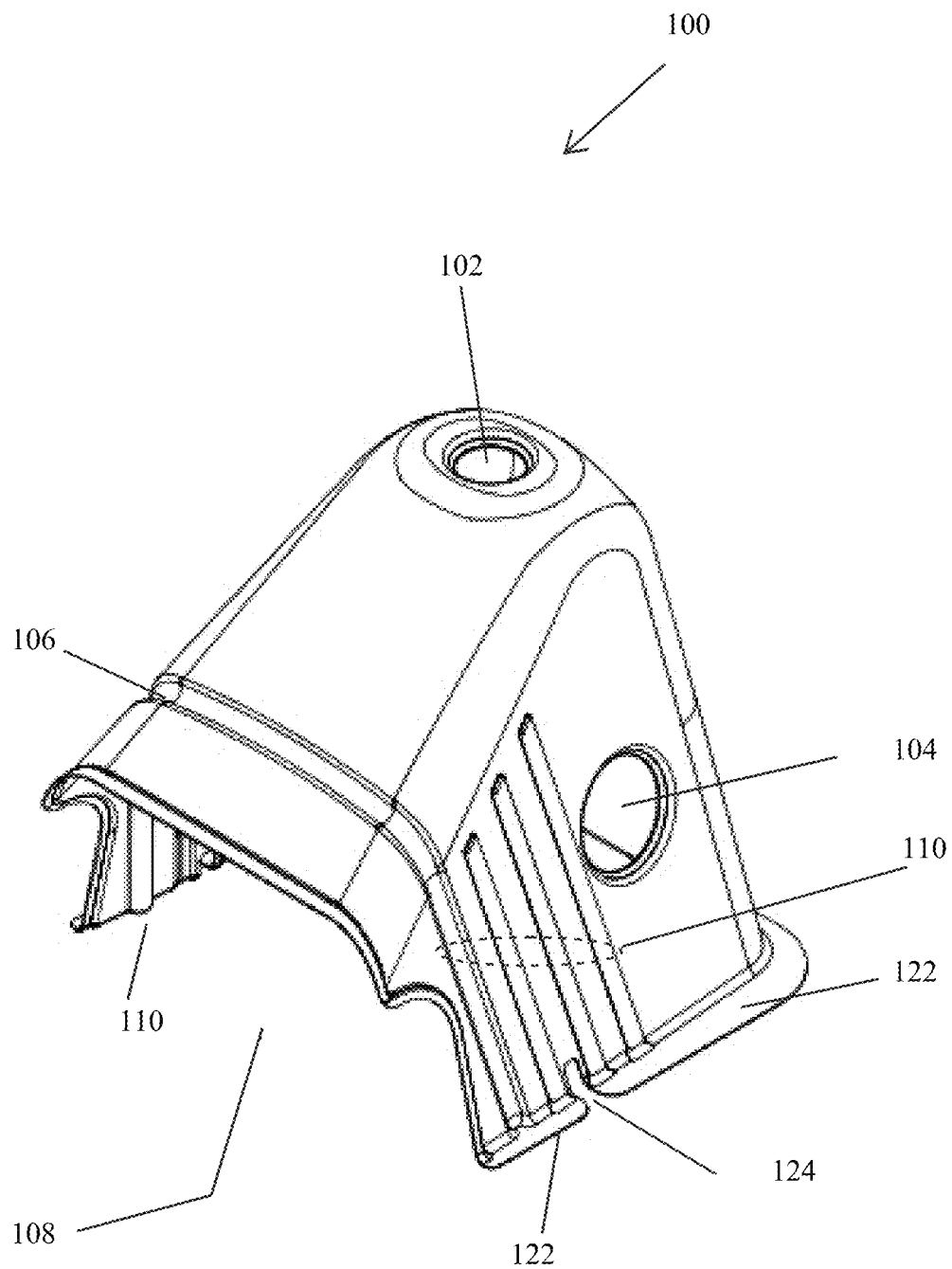
FIG. 1 shows a perspective view.
Figure 3:
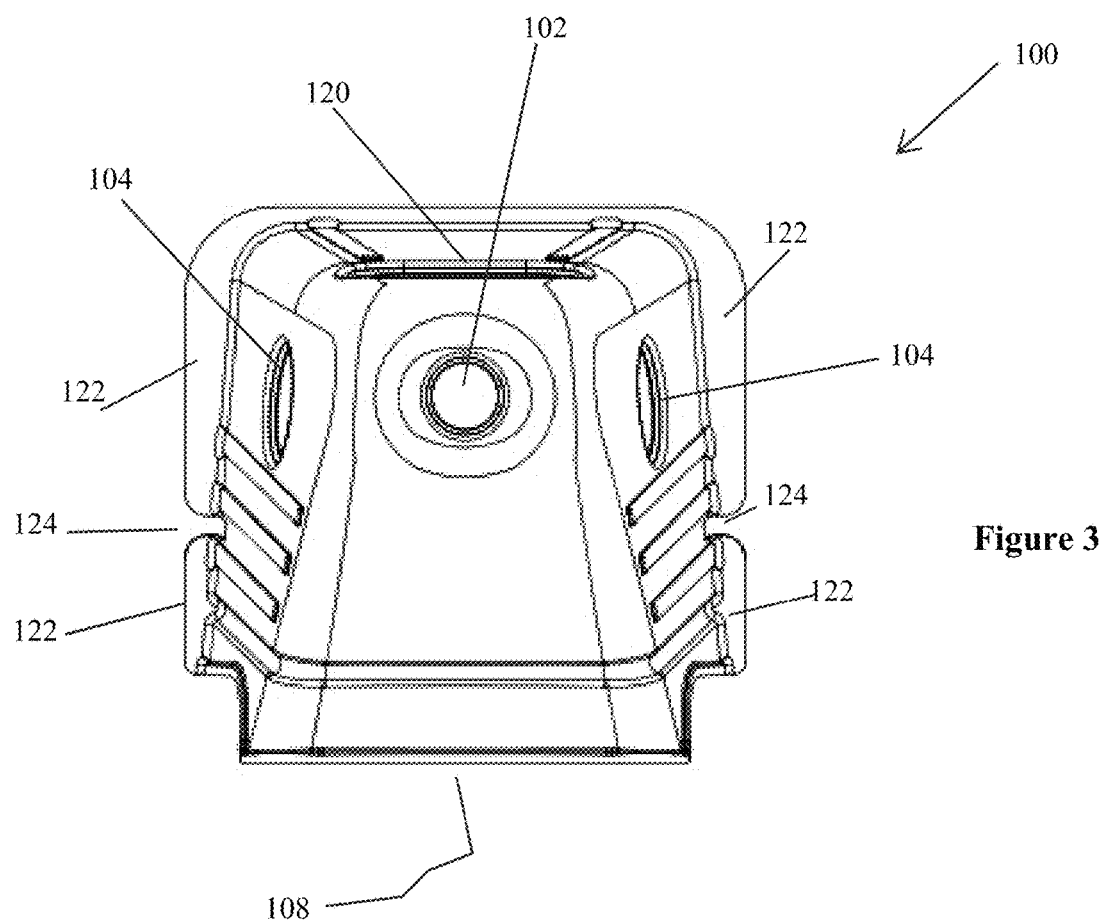
FIG. 3 is a bottom view, revealing an interior.

FIG. 1 shows a perspective view of the shield 100. Distinctive pyramidal shape of the shield 100 promotes the flow of warm air upwards via what is commonly referred to as the chimney effect, to be removed from the shield 100 via vent 102. Vent 102 is provided with a top cap 103 (FIGS. 7A, 7B, 8A, 8B, and 9) to which specific venting equipment may be attached to draw air out of the interior of shield 100. Side ports 104, on left and right side, allow assisting clinicians to place their hands inside the shield 100, in order to assist in adjusting equipment and about patient 202 (FIG. 3). Side ports 104 are configured with a flexible seal that allows hand and forearm to be inserted, but also inhibit leaking of air from inside shield 100. Drape coupling 106 comprises a fastener using adhesive, hook-and-loop, elastic, and other methods for holding a drape (for example, plastic or cloth) in place and providing a loose seal to inhibit leaking of air from inside shield 100. Distinctive shape of the shield 100 further provides opening 108, accommodating the torso of patient 202 (FIG. 3). Notch 124 serves at least two purposes. One purpose is to provide entry points for ventilation tubing and cabling required to serve patient 202. Another purpose is to provide an entry point for outside cooler air to be drawing in as warmer, potentially contaminated air, is drawn out through vent 102 and top seal 103. Brim 122 is a surface, generally perpendicular to the general orientation of shield 100, providing support for resting shield 100 securely on a hospital bed, gurney, table, or other patient bearing structure.

Figure 2:
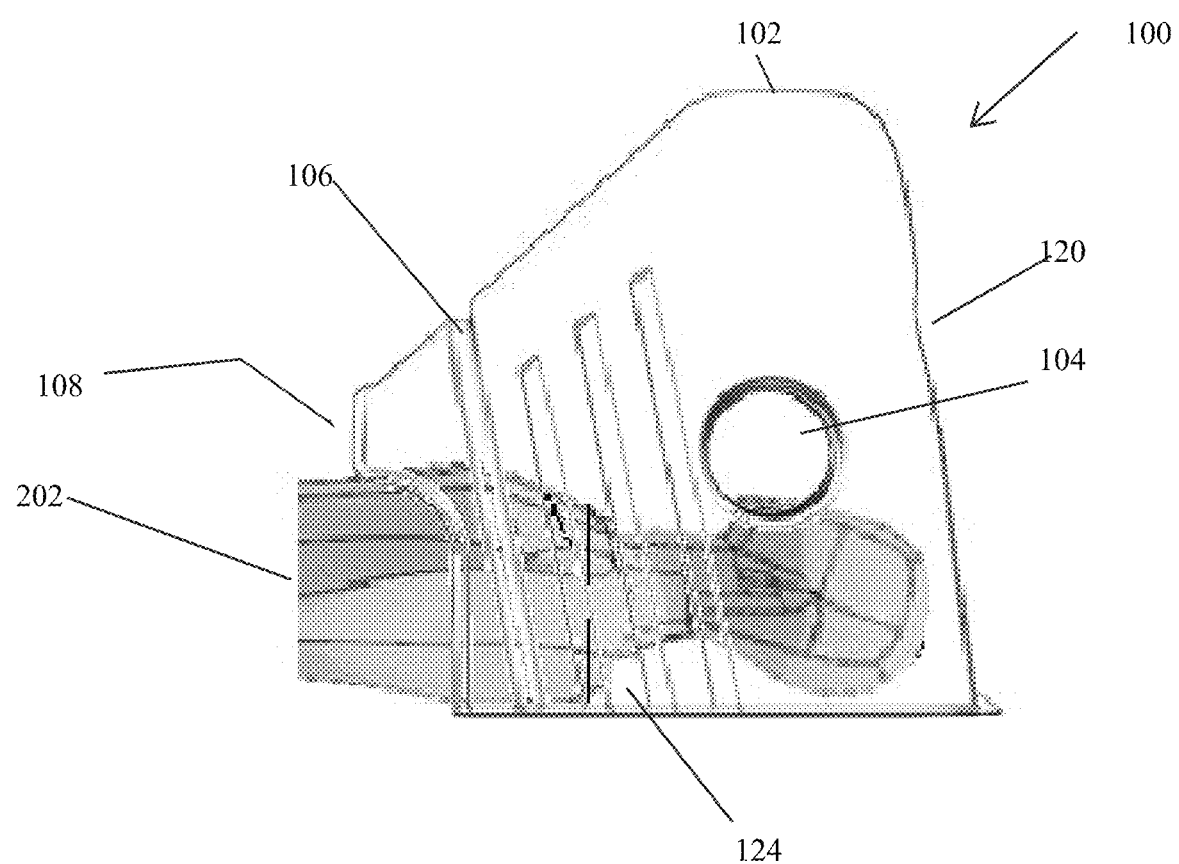
FIG. 2 is a side view, with patient.

FIG. 2 is a side view of shield 100, showing general placement of patient 202 inside the shield. Rear port 120 is not directly visible in FIG. 2; however, its location is indicated, for reference.

Figure 6:
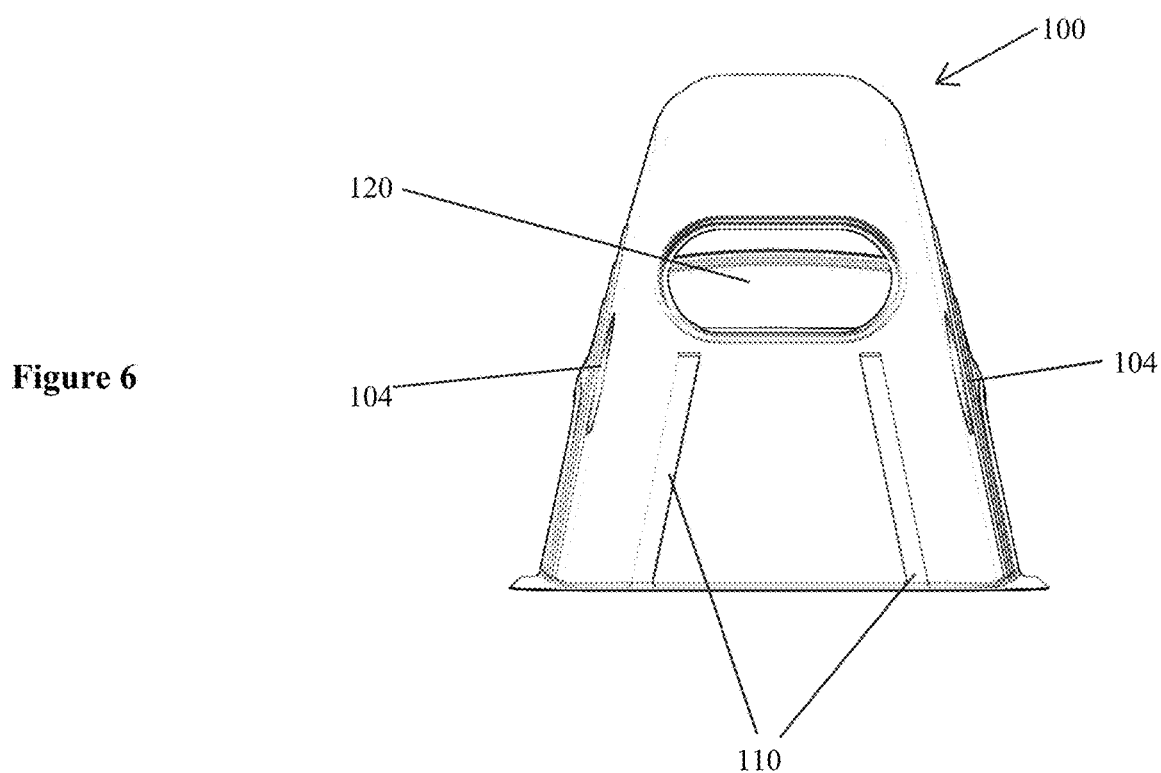
FIG. 6 is a rear view.

FIG. 3 is a bottom view into shield 100 interior, providing additional views of the placement of vent 102, side ports 104, notch 124, opening 108, brim 122, and rear port 120 (more substantially depicted in FIG. 6.

Figure 4:
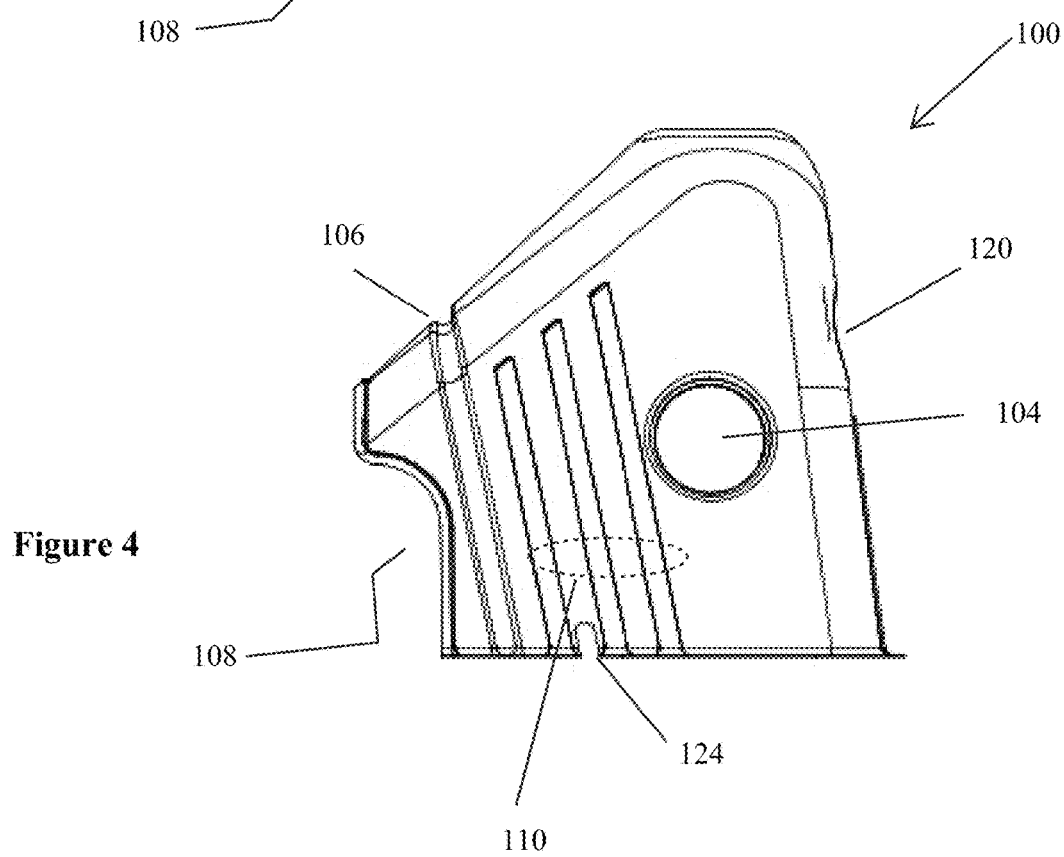
FIG. 4 is a left side view.

FIG. 4 is a left side view of shield 100, and representative also of a right-side view.

Figure 5:
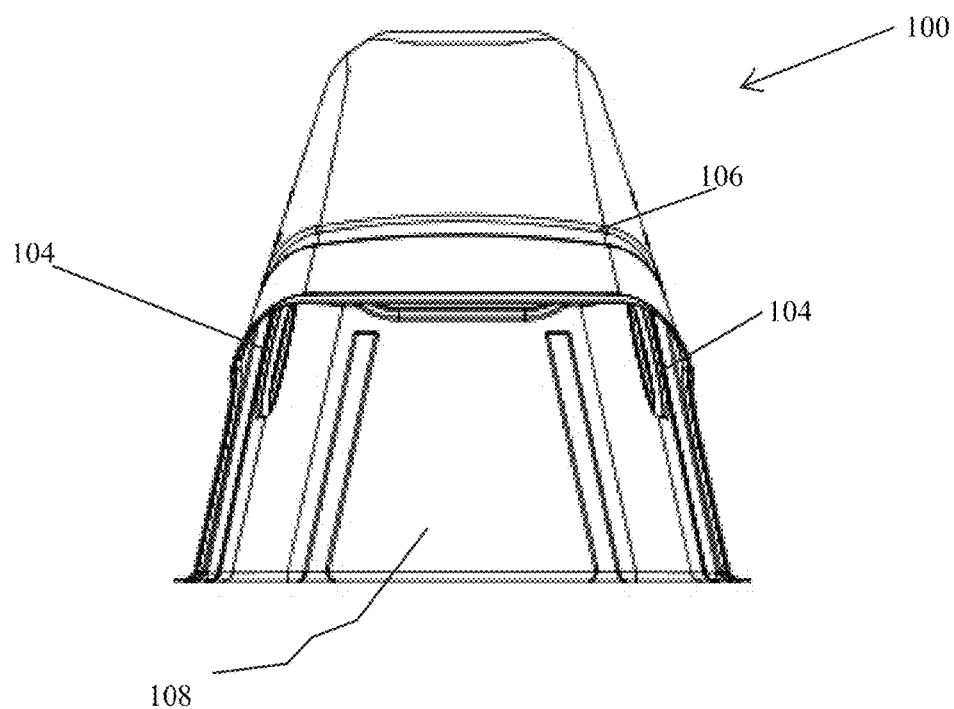
FIG. 5 is a front view, further revealing the interior.

FIG. 5 is a front view of shield 100, revealing the interior into which the patient's 202 head and torso are placed.

FIG. 6 shows rear 120, which is distinctive in that it is a single, elongated port allowing convenient movement of forearm and hands of the primary clinician. Use of two smaller ports would unnecessarily restrict clinician hand movement, thus adding to patient 202 risk. As with side ports 104, rear port 120 is configured with a seal that allows hands and forearms to be inserted, but also inhibiting the leaking of air from inside shield 100.

Figure 7A:
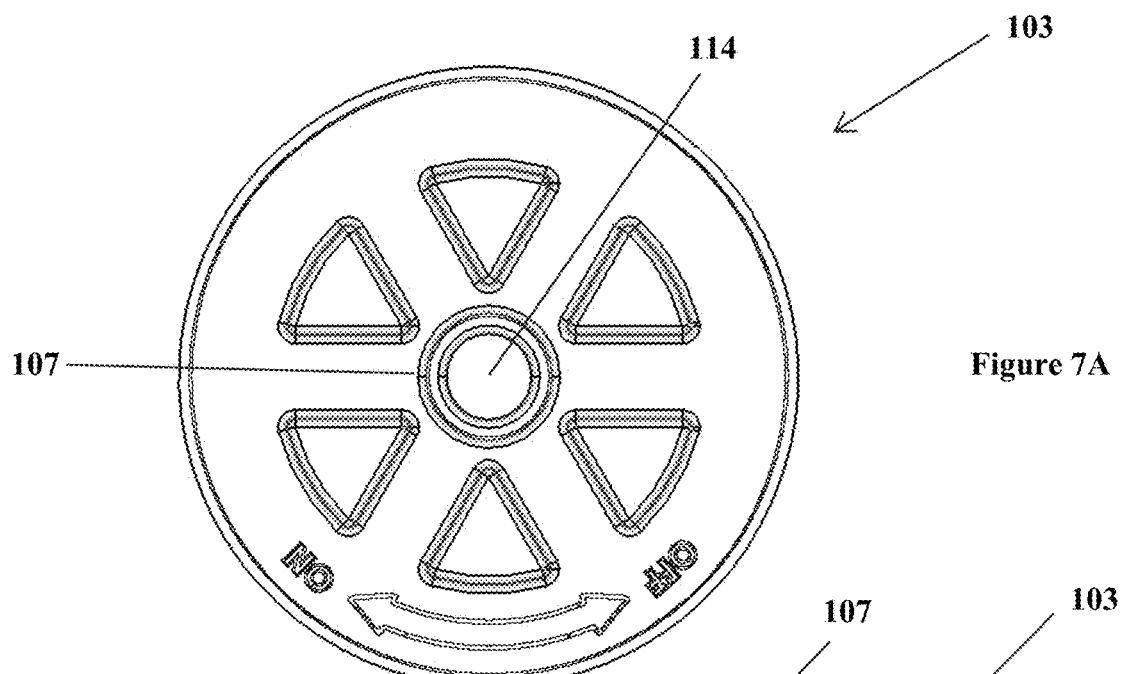
FIGS. 7A and 7B show a top cap, with top side and underside respectively.
Figure 7B:
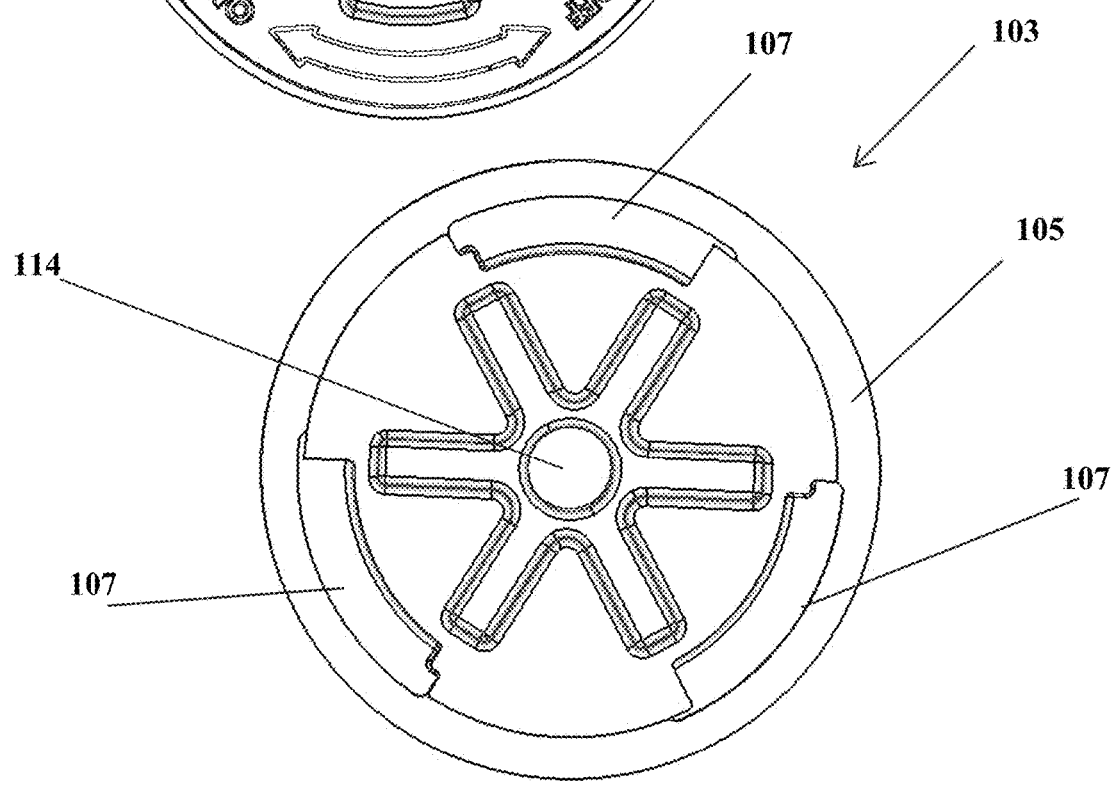

FIGS. 7A and 7B show, respectively, the top side and underside of top cap 103. FIG. 7A shows further a top view of a port 109 as part of the top cap 103, and corresponding hole 114 in top cap 103 through which air inside shield 100 would be expelled. FIG. 7B, the underside of top cap 103, shows hole 114 and also shows three locking ears 107 used to secure the top cap 103 onto vent 102. Rotating top cap 103, when it is inserted onto vent 102, causes each locking ear 107 to engage a corresponding ramp on the vent 102 to secure the top cap 103 in place. Opposite rotation of the top cap 103 will disengage the locking ears 107, and allow the top cap 103 to be removed. Furthermore, FIG. 7B shows an O-ring 105, used as a seal or gasket to inhibit contaminated air inside shield 100 from escaping except through port 109, filter 111, and too cap 103.

Figures 8A, 8B:
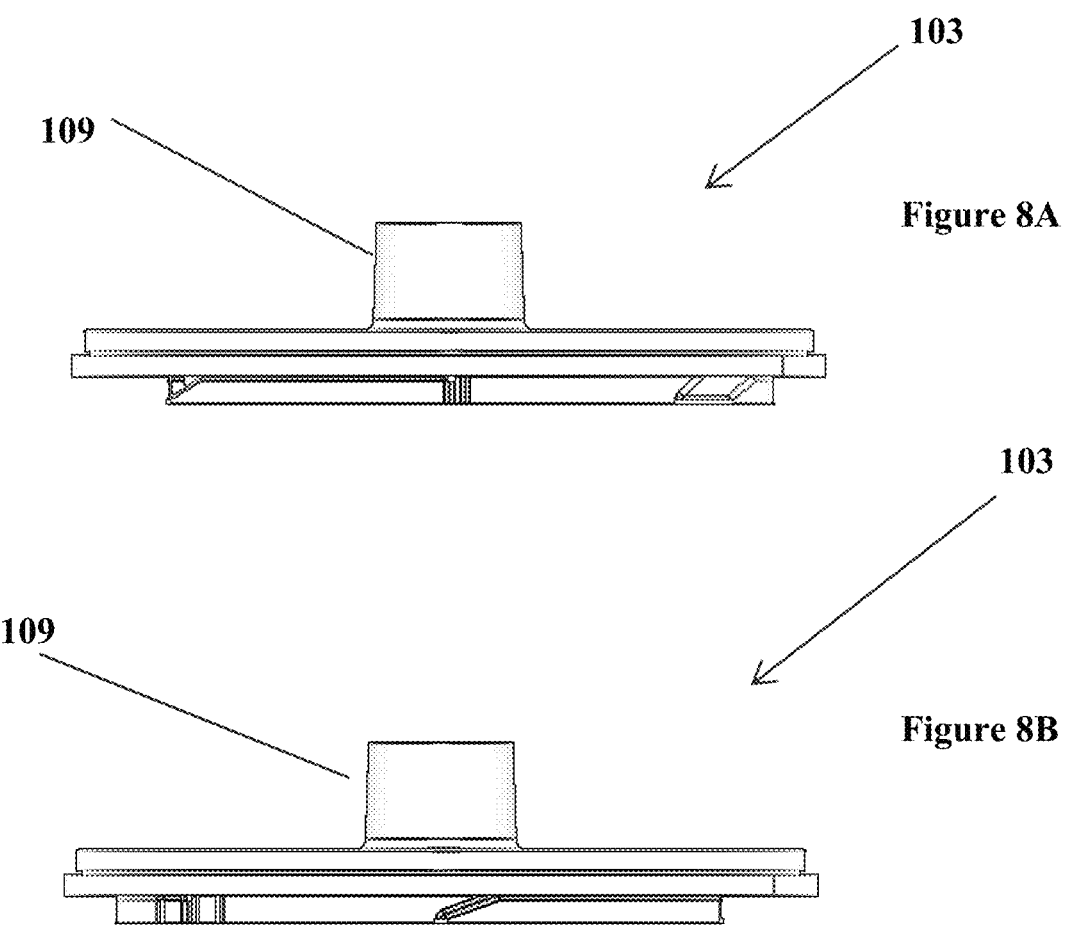
FIGS. 8A and 8b show profile view for the top cap.

FIGS. 8A and 88 show side views to top cap 103, and further showing port 109 as a protrusion through which contaminated air is drawn out of the shield 100.

Figure 9:
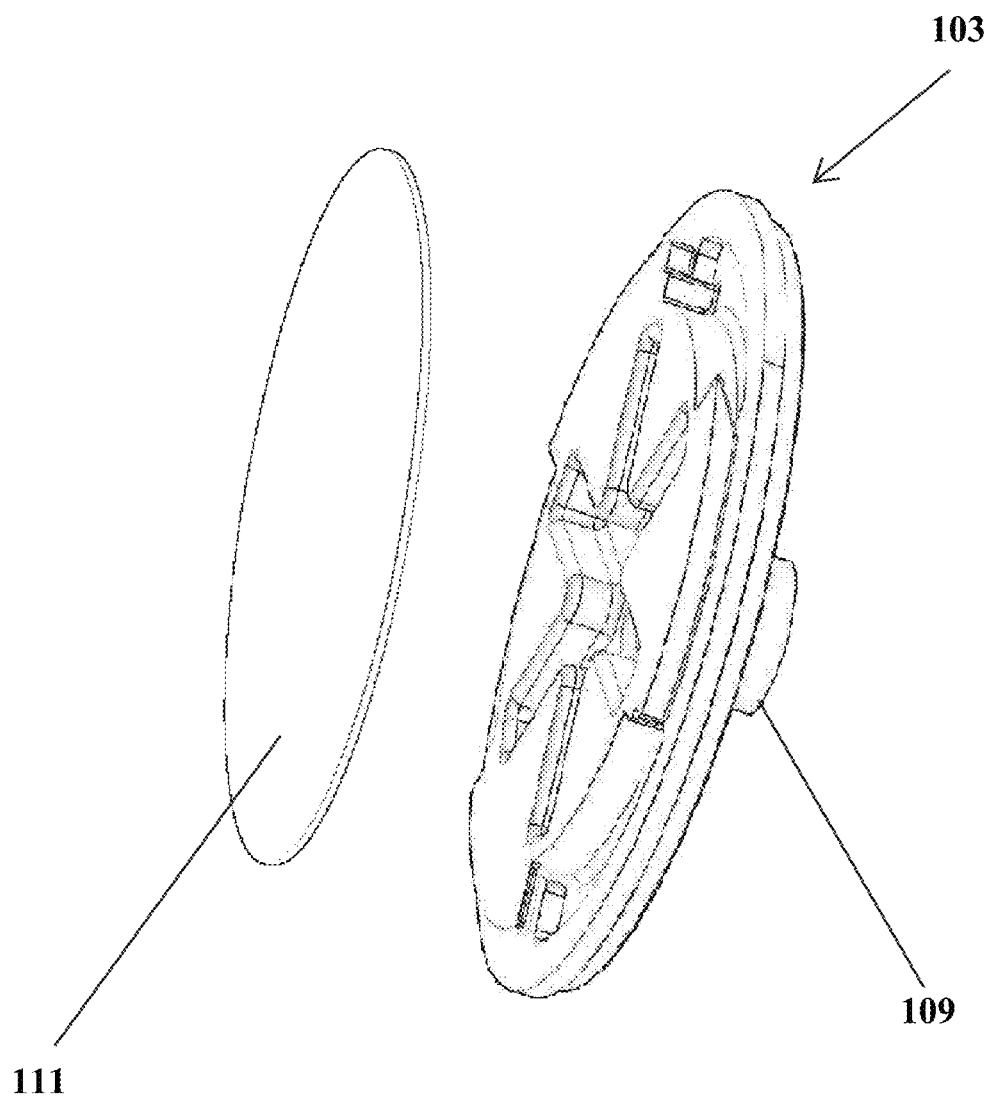
FIG. 9 shows an exploded view of the top cap and associated filter.

FIG. 9 shows an exploded view of top cap 103 and filter 111. The filter will further treat aerosolized bacteria, viruses, carbon dioxide, and other contaminants on their way out of the shield 100 and into whatever contaminant processing is provided.

BEST MODE OF THE PREFERRED EMBODIMENT

FIG. 2 depicts a best mode of operation, with patient 202 on his or her back on a bed or table, and shield 100 placed to cover torso and head. A primary clinician would operate from the rear, while assistant clinicians would assist from left and right side. Use of a drape is optional, as is use of equipment at vent 102 to assist in drawing air from shield 100. Not shown in FIG. 2, but part of the best mode is use of the top cap 103 with filter 111 to facilitate removal of aerosolized contaminants.

Best mode shows a generally pyramidal shape, being wider at the bottom (closer to the patient 202) than at the top. Alternative shapes also promoting air flow upward to a vent include generally conical, hemispherical, or multifaceted approximations thereof.

Similarly, more than one vent may be configured for efficient and safe expulsion of air from inside the shield 100.

Advantages

Advantages if the shield 100 as described and claimed include:
  light weight, but sufficiently rigid
  quickly deployable
  antimicrobial protection
  elongated rear port
  top venting
  single use, and reusable
  pyramidal shape allows for convenient stacking for storage and shipping
  port seals and drape accommodation to inhibit air leakage While the foregoing written description enable one of ordinary skill to make and use what is considered presently to be the best mode thereof, those of ordinary skill will understand and appreciate the existence of variations, combinations, and equivalents of the specific embodiment, methods, and examples herein.

I claim:

1. A hospital bed shield for protecting clinicians from aerosolized bacteria and viruses, comprising
 a shape formed from transparent materials, said transparent materials embedded with antimicrobial treatment;
 one or more side ports;
 one or more elongated rear ports;
 one or more vents;
 a top cap for each said vent,
  said too can further having one or more locking ears:
 a filter for each said top cap;
 one or more notches;
 and
 drape coupling.

2. The hospital bed shield of claim 1, wherein the shape is generally pyramidal.

3. The hospital bed shield of claim 1, wherein the shape is generally conical.

4. The hospital bed shield of claim 1, wherein the shape is generally hemispherical.

5. The hospital bed shield of claim 1, wherein the shape is generally multifaceted.

* * * * *